US00PP12945P2

(12) United States Plant Patent
Hanes

(10) Patent No.: US PP12,945 P2
(45) Date of Patent: Sep. 10, 2002

(54) GERANIUM PLANT NAMED 'CLIPS VIO'

(75) Inventor: Mitchell Eugene Hanes, Morgan Hill, CA (US)

(73) Assignee: Goldsmith Plants Inc., Gilroy, CA (US)

( * ) Notice: Subject to any disclaimer, the term of this patent is extended or adjusted under 35 U.S.C. 154(b) by 39 days.

(21) Appl. No.: 09/802,870

(22) Filed: Mar. 12, 2001

(51) Int. Cl.[7] ..... A01H 5/00

(52) U.S. Cl. ..... Plt./329

(58) Field of Search ..... Plt./324, 329

*Primary Examiner*—Bruce R. Campell
*Assistant Examiner*—June Hwu
(74) *Attorney, Agent, or Firm*—Rothwell, Figg, Ernst & Manbeck

(57) ABSTRACT

A geranium cultivar particularly distinguished by dark green foliage with light zonation, violet flower color, and semi-double flowers on large umbels, fast rooting and exhibits vigorous growth.

1 Drawing Sheet

GENUS AND SPECIES

*Pelargonium hortorum.*

VARIETY DENOMINATION

Figure 1:
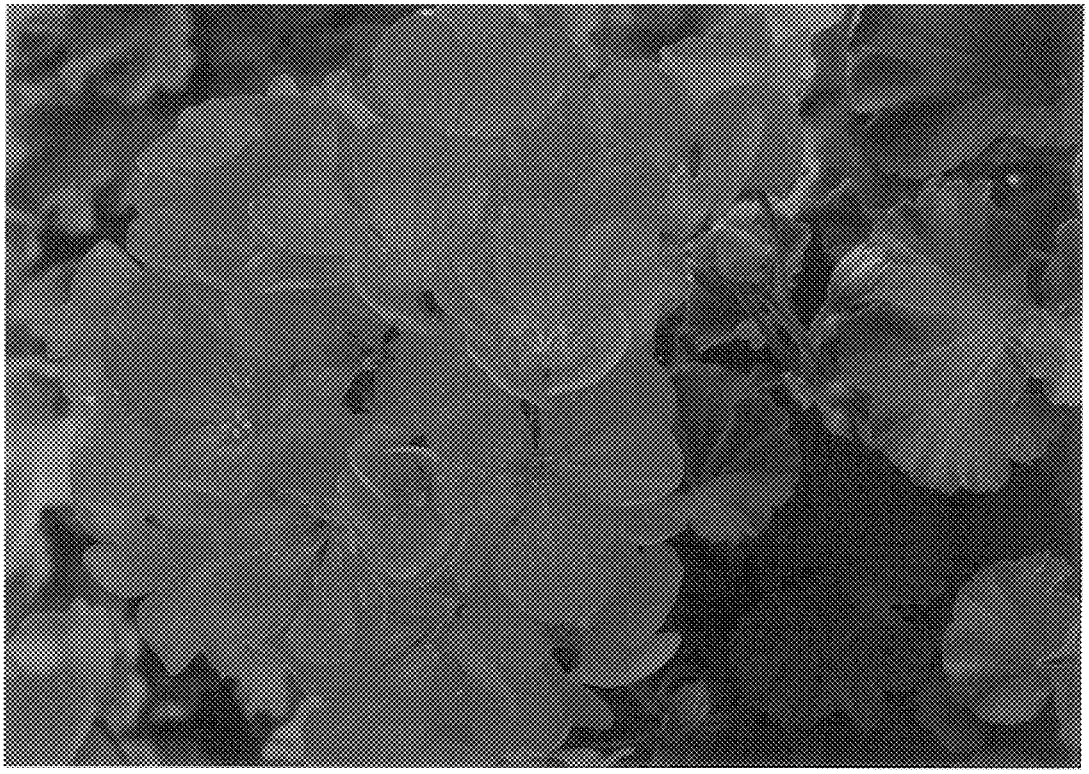

'Clips Vio'.

BACKGROUND OF THE NEW PLANT

The present invention comprises a new and distinct cultivar of geranium, botanically known as *Pelargonium hortorum* Bailey, and hereinafter referred to by the cultivar name 'Clips Vio'. The new cultivar is propagated from a seedling resulting from the cross of an unnamed and unpatented seed parent known as 7149-1 which is a bright rose single flower line and an unnamed and unpatented pollen parent known as 6365-2 which is a blue rose flowered and dark leafed plant.

'Clips Vio' is a product of a planned breeding program intended to create new geranium cultivars with violet colored flowers, semi-double flower form, dark green foliage, vigorous growth and superior cutting productivity.

The new cultivar was created in 1996 in Gilroy, Calif. and has been repeatedly asexually reproduced by cuttings in Gilroy, Calif. and Guatemala over a four year period. It has also been trialed at Gilroy, Calif. and Andijk, The Netherlands. It has been found to retain its distinctive characteristics through successive propagations; and this novelty is firmly fixed.

DESCRIPTION OF PHOTOGRAPH

This new geranium plant is illustrated by the accompanying photograph which shows blooms, buds, and foliage of the plant in full color, the colors shown being as true as can be reasonably obtained by conventional photographic procedures.

FIG. 1 shows overall plant habit.

DESCRIPTION OF THE NEW CULTIVAR

The following detailed descriptions set forth the distinctive characteristics of 'Clips Vio'. The data which defines these characteristics were collected from asexual reproductions carried out in Gilroy, Calif. The plant history was taken on five month old plants grown in 8 inch pots, blossomed under natural light in a greenhouse and color readings were taken in the greenhouse in Gilroy, Calif. under ambient light. Color references are primarily to The R.H.S. Colour Chart of The Royal Horticultural Society of London (R.H.S.).

DETAILED BOTANICAL DESCRIPTION

Classification:
*Botanical.*—*Pelargonium hortorum* Bailey.
*Commercial.*—Geranium.
Form: Upright, rounded plant.
Height: From soil level to top of plant (excluding blooms) — 20 cm; from soil level to top of umbels — 30 cm.
Width: 30–35 cm.
Time to produce a finished flowering plant: 12 weeks.
Outdoor plant performance: Good heat tolerance, strong growth, maintains rounded habit.
Time to initiate roots: 7–8 days.
Time to develop roots: 25 days.
Root description: White, fibrous yet coarse, slightly hairy.

The Leaves

Length: 4.8–5.5 cm.
Width: 7.0–8.5 cm.
Apex measurement: 5.0–6.0 cm.
Base measurement: 7.0–8.0 cm.
Shape: Reniform.
Margin: Irregularly crenate.
Texture: Leathery and pubescent on both surfaces.
Ribs and veins: Palmate, 3.0–5.0 cm long.
Color:
*Upper side.*—Green RHS 137A.
*Under side.*—Yellow-green RHS 147B.
*Ribs.*—Yellow-green RHS 146D.
*Veins.*—Some are Green RHS 137B and some are yellow-green RHS 146D.
Petiole length: 4.0–6.0 cm.
Petiole diameter: 2.0–3.0 mm.
Petiole color: Yellow-green RHS 146B.
Lateral branch length: 6.0–9.0 cm.
Internode length: 1.5–3.0 cm.
Lateral branch color: Yellow-green RHS 146A.

The Bud

Diameter: 7 mm.
Length: 1.4 mm.
Shape: Narrow elliptic.
Color when sepals first divide: Red purple RHS 67A.
Number of sepals: 5 linear-lanceolate shaped.
Length of sepals: 1 cm.
Width of sepals: 3 mm.
Apex shape: Mucronate.
Base shape: Truncate.
Sepal color: Upper and lower are yellow-green RHS 146B; 1 mm of the bottom sepal base is red purple RHS 60A.

The Flower

Bloom season: Continuous throughout the year in greenhouse or Zone 9 climate.
Size: Approximately 4.7 cm in diameter.
Form: Polypetalous, semi-double, cup shaped when first open, later flattening to shallow cup shape.
Petals/petaloids: 6 petals, 2–3 petaloids; Shape: spatulate, 1.5 cm wide and 2.2 cm long.
Apex shape: Obtuse-retuse.
Base shape: Attenuate.
Margin: Entire.
Petal color:
*Upper surface.*—Red-purple RHS 66A with a "flare" of red RHS 43A and stripes of red-purple RHS 67A.
*Lower surface.*—Red-purple RHS 66B with occasional white RHS 155D stripes.
Surface texture of petals and petaloids: Papillose (satiny).
Petaloid color:
*Upper surface.*—Red-purple RHS 66A.
*Lower surface.*—Red-purple RHS 66A.
Color change with age: None.
Pedicel length: Approximately 3 cm.
Pedicel color: Yellow-green RHS 146C with an occasional stripe of red-purple RHS 66B.
Flower persistance: An open flower will hold it's petals until the flower begins to dehisce, or approximately 7–10 days.

The Inflorescence

Type: An umbel composed of approximately 25 flowers.
Diameter: 10 cm.
Depth: 6.5 cm.
Peduncle length: 13–16 cm.
Peduncle color: Yellow-green RHS 148B with speckles of red-purple RHS 67A.

The Reproductive Organs

Anthers 10.
Anther color: Red-purple RHS 66A prior to anthesis.
Filament color: White RHS 155D graduating to red-purple RHS 66A near anther.
Lengths of anthers and filaments: Anther — 0.3 cm; filament 0.8–0.9 cm.
Pollen amount and color: Moderate orange RHS 26A.
Pistil: 1 with a length of 8 mm.
Stigma: 5 linear lobes of near equal length curling back toward ovary with a color of red-purple RHS 66A.
Style: 3 mm with a color of red-purple RHS 60A.
Ovary: Densely pubescent with white hairs, oblong, inferior.
Seed number: Maximum of 5 per spike.
Seed length: 3.0–4.0 mm.
Seed width: 1.0 mm.
Seed color: Brown RHS 165A; may darken with age.

Disease and Insect Resistance

No susceptibility to diseases or insects noted to date.

Comparison with Known Cultivars

When 'Clips Vio' is compared to both 7149-1 and 6365-2, 'Clips Vio'has a darker purple flower color and is also more basal branching than these two cultivars.

I claim:

1. A new and distinct cultivar of geranium plant as shown and described herein.

* * * * *